US009863896B2

(12) United States Patent
Matoba

(10) Patent No.: US 9,863,896 B2
(45) Date of Patent: Jan. 9, 2018

(54) X-RAY TRANSMISSION INSPECTION APPARATUS

(71) Applicant: Hitachi High-Tech Science Corporation, Minato-ku, Tokyo (JP)

(72) Inventor: Yoshiki Matoba, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 128 days.

(21) Appl. No.: 14/674,133

(22) Filed: Mar. 31, 2015

(65) Prior Publication Data

US 2015/0276626 A1 Oct. 1, 2015

(30) Foreign Application Priority Data

Mar. 31, 2014 (JP) ................. 2014-072912

(51) Int. Cl.
*G01B 15/06* (2006.01)
*G01N 23/083* (2006.01)
*G01N 23/16* (2006.01)
*G01N 23/04* (2006.01)

(52) U.S. Cl.
CPC ......... *G01N 23/083* (2013.01); *G01N 23/043* (2013.01); *G01N 23/16* (2013.01); *G01N 2223/04* (2013.01); *G01N 2223/505* (2013.01); *G01N 2223/642* (2013.01); *G01N 2223/652* (2013.01)

(58) Field of Classification Search
CPC ......... G01N 2223/04; G01N 2223/505; G01N 2223/642; G01N 2223/652; G01N 23/043; G01N 23/083; G01N 23/16; G01N 21/9501; G01N 21/94; G01N 2223/3307; G01N 2021/8822; G01N 2201/1211; G01N 2201/1218; G01N 21/95623; G01N 2201/0231; G01N 21/95607; G01N 2021/95676; G01N 21/956; G01N 2021/8905
USPC ................ 378/10, 160, 146–153; 250/370.1
See application file for complete search history.

(56) References Cited

U.S. PATENT DOCUMENTS

2009/0310738 A1* 12/2009 Tischenko ............ G01T 1/2985
378/10
2013/0032728 A1* 2/2013 Matoba ................ G01N 23/083
250/394

FOREIGN PATENT DOCUMENTS

JP H08-266531 A 10/1996
JP 2004-061479 A 2/2004

* cited by examiner

*Primary Examiner* — Irakli Kiknadze
(74) *Attorney, Agent, or Firm* — Banner & Witcoff, Ltd.

(57) ABSTRACT

An X-ray transmission inspection apparatus includes: an X-ray source configured to irradiate a sample with an X-ray; a detector configured to be disposed on a side opposite to the X-ray source with respect to the sample and to detect the X-ray which is transmitted through the sample using a phosphor; a shield member configured to be arranged to face a detection surface of the detector and to block a part of X-rays to partially form a shield area from the X-rays on the detection surface; and a shield moving mechanism configured to move the shield member relative to the detector to enable change of a position of the shield area.

6 Claims, 2 Drawing Sheets

X-RAY TRANSMISSION INSPECTION APPARATUS

CROSS-REFERENCE TO RELATED APPLICATION

This application claims priority from Japanese Patent Application No. 2014-072912, filed on Mar. 31, 2014, the entire subject matter of which is incorporated herein by reference.

BACKGROUND

1. Technical Field

The present invention relates to an X-ray transmission inspection apparatus that enables detection of a metallic foreign substance and the like in a sample.

2. Description of the Related Art

Generally, an X-ray transmission inspection (X-ray radiographic inspection) has been used in order to detect a metal foreign substance in a sample, unevenness of the thickness of the sample, or the like. The X-ray transmission inspection is performed using a fluoroscopic image obtained by irradiating a sample with an X-ray. In an apparatus used in the X-ray transmission inspection, when an inline type inspection for a sample having a belt shape is performed, normally, a product (sample) flowing in one direction is disposed inbetween, and an X-ray generator that generates an X-ray and a line sensor that detects the X-ray are disposed to face each other.

For example, JP-A-2004-061479 discloses an X-ray foreign substance detector that includes a multi-stage X-ray generator, a multi-stage X-ray detector, and a multi-stage beam limiting device or a blocking plate. The multi-stage beam limiting device or a blocking plate is provided such that the X-ray detector in another region is not irradiated with an X-ray emitted from the X-ray generator.

The technique of the related art may have the following problems.

That is, in a foreign substance detection apparatus of the related art using X-ray transmission, a high spatial resolution is required in order to perform fine detection and it is consequentially necessary that a resolution of a sensor (detector) that detects an X-ray increases. Increasing the resolution of the sensor means that a pixel size of the sensor is reduced. However, if the pixel size of the sensor is reduced, the number of X-rays which are incident to a pixel in proportion to a pixel area is reduced. If the number of the X-rays is reduced, a ratio of a noise in the fluoroscopic image in statistical fluctuation of X-rays becomes larger and the noise in the fluoroscopic image becomes a problem. For this reason, it is generally considered that, for example, an output of an X-ray generator is improved and thus the number of incident X-rays itself increases. However, if the number of incident X-rays increases, it is inconvenient that a phosphor in a sensor that detects an X-ray is rapidly deteriorated due to X-rays and it is impossible to maintain performance until a predefined lifespan. If a sensor is deteriorated, exchange of the sensor or stopping application of an X-ray is required and a downtime of the apparatus becomes a problem in a case where a full time operation is necessary around the clock.

SUMMARY

The present invention has been made in view of the above-described circumstances, and one of objects of the present invention is to provide an X-ray transmission inspection apparatus that is able to reduce a downtime of an apparatus and to obtain a long lifespan of an X-ray detector.

According to an exemplary embodiment of the present invention, there is provided an X-ray transmission inspection apparatus including: an X-ray source configured to irradiate a sample with an X-ray; a detector configured to be disposed on a side opposite to the X-ray source with respect to the sample and to detect the X-ray which is transmitted through the sample using a phosphor; a shield member configured to be arranged to face a detection surface of the detector and to block a part of X-rays to partially form a shield area from the X-rays on the detection surface; and a shield moving mechanism configured to move the shield member relative to the detector to enable change of a position of the shield area.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Hereinafter, a first embodiment of an X-ray transmission inspection apparatus according to the present invention will be described with reference to FIG. 1.

Figure 1:
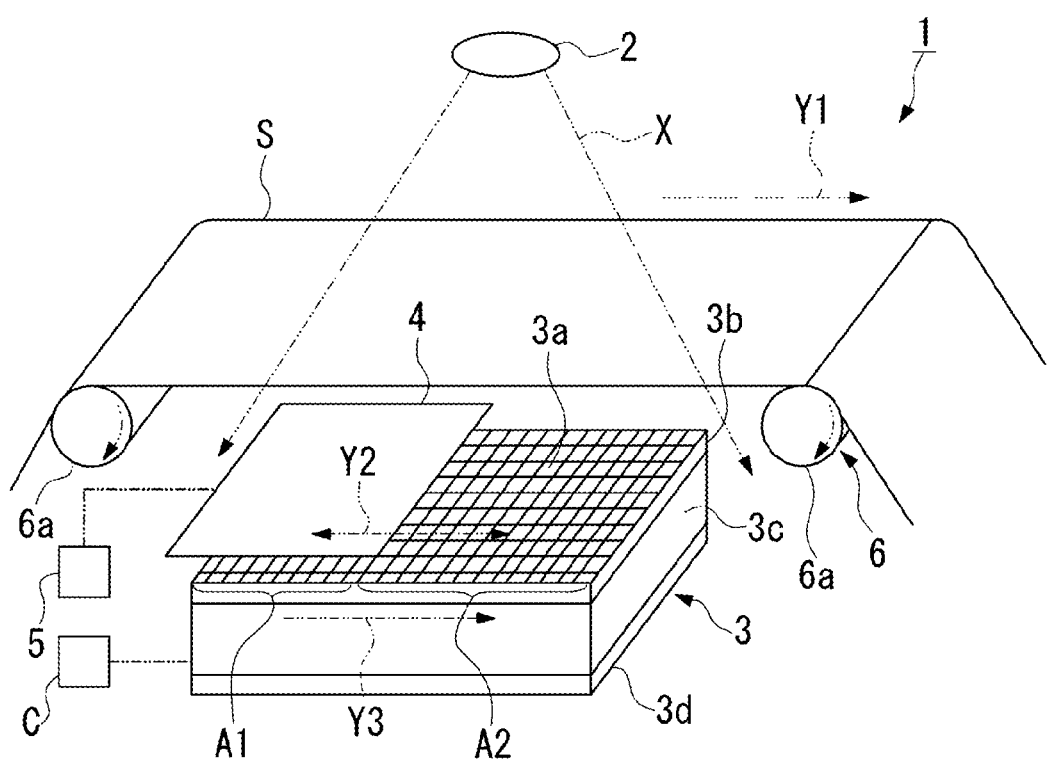
FIG. 1 is an overall configuration diagram schematically illustrating a first embodiment of an X-ray transmission inspection apparatus according to the present invention.

The X-ray transmission inspection apparatus 1 according to the first embodiment is provided with an X-ray source 2, a detector 3, a shield member 4, a shield moving mechanism 5, and a sample moving mechanism 6, as illustrated in FIG. 1. The X-ray source 2 irradiates a sample S having a belt shape with an X-ray X. The detector 3 is disposed on a side opposite to the X-ray source 2 based on the sample S and uses a phosphor 3b for detecting the X-ray X which is transmitted through the sample S. The shield member 4 is arranged to face a detection surface 3a of the detector 3 and blocks some of X-rays X to partially form a shield area A1 from the X-rays X on the detection surface 3a. The shield moving mechanism 5 moves the shield member 4 relative to the detector 3 to enable change of a position of the shield area A1. The sample moving mechanism 6 enables the sample S to be moved in a longitudinal direction.

The X-ray transmission inspection apparatus 1 further includes a control unit C that controls the detector 3 and detects a foreign substance corresponding to received X-rays X.

The sample S is a material for an Li-ion battery, which is formed to have a belt shaped or a material used in a pharmaceutical field, for example.

The X-ray source 2 is configured by an X-ray tube bulb that enables emission of an X-ray and emits an X-ray X from a window formed from a beryllium foil. In the X-ray source 2, a voltage which is applied between a filament (cathode) and a target (anode) causes thermoelectrons which are generated from the filament (cathode) in the tube bulb to accelerate and collide with W (tungsten), Mo (molybdenum), Cr (chrome), and the like of the target and thereby the X-ray is generated.

The detector 3 is configured by a TDI (Time Delay Integration) sensor. The TDI sensor includes phosphors 3b which are arranged on the detection surface 3a, an FOP (fiber optics plate) 3c which arranges a plurality of optical fibers two-dimensionally in a matrix form to have a plurality of rows under the phosphors 3b, and an Si light reception element 3d which is arranged under the FOP 3c. The TDI sensor has a structure in which line sensors are arranged to have a plurality of rows. For example, unit line sensors at 200 to 1000 stages are arranged in a feeding direction of the sample S so as to constitute the TDI sensor (detector 3).

The TDI sensor uses the phosphors 3b such as CsI (cesium iodide), GOS (gadolinium oxysulfide), and YAG (yttrium aluminum garnet).

The control unit C is connected to each mechanism, the X-ray source 2, the detector 3, and the like, and is configured by a computer configured by a CPU which controls these, and the like.

The control unit C has a function of causing a charge transfer direction and speed in the TDI sensor (detector 3) to match with a moving direction and speed of the sample S and of summing luminance values of the X-rays X received by the TDI sensor depending on an area (detection area A2) other than the shield area A1 shielded by the shield member 4. That is, the control unit C sets the charge transfer speed (feeding speed) VTDI of the TDI sensor (detector 3) in the detection area A2 to be the same as the speed VS of the sample S, and controls flowing of the sample S and a summing process of the TDI sensor to be synchronized.

The shield member 4 is configured by a plate-shaped member formed of a material through which the X-ray X is not transmitted. For example, Pb (lead), W (tungsten), SUS (stainless steel), and the like are used for the shield member 4.

The shield moving mechanism 5 is configured by a motor and the like which enables the shield member 4 to be moved relative to the detector 3 in the longitudinal direction of the sample S.

The shield moving mechanism 5 has a function of changing a position of the shield area A1 at a constant interval. For example, the shield moving mechanism 5 may be set such that the position of the shield area A1 is automatically changed at a time interval such as a day or a month.

The sample moving mechanism 6 includes at least one pair of rollers 6a which moves the sample S having a belt shape in the longitudinal direction in a roll-to-roll manner. That is, the sample S bridges over the pair of rollers 6a which are disposed to be parallel and the rollers 6a are cause to drive and rotate. Thus, the sample S is moved in one direction. The X-ray source 2, the shield member 4, and the detector 3 are disposed in a region between the pair of rollers 6a.

An arrow Y1 in FIG. 1 indicates the moving direction of the sample S, an arrow Y2 indicates a moving direction of the shield member 4, and an arrow Y3 indicates a TDI driving direction of the TDI sensor (detector 3).

The X-ray transmission inspection apparatus 1 according to such the first embodiment includes the shield member 4 that blocks some of X-rays X to partially form the shield area A1 from the X-rays X on the detection surface 3a, and the shield moving mechanism 5 that moves the shield member 4 relative to the detector 3 to enable change of a position of the shield area A1. Thus, the detection area A2 and the shield area A1 on the detection surface 3a which are irradiated with the X-ray X are shifted with time by moving the shield member 4, and thus it is possible to restore the phosphor 3b in the shield area A1 during a time when an inspection is performed using the detection area A2.

That is, although the phosphor 3b in the detection area A2 which is irradiated with the X-ray X is deteriorated and the luminous intensity is lowered, the shield moving mechanism 5 causes the detection area A2 and the shield area A1 to be shifted with time, and thus it is possible to anneal the deteriorated phosphor 3b in the shield area A1 and to restore the luminous intensity of the phosphor 3b.

Since the detector 3 is configured by the TDI sensor and the shield moving mechanism 5 enables the shield member 4 to be moved in the longitudinal direction of the sample S, it is possible to improve sensitivity to be the number of stages times by using the TDI sensor that enables summation of values by the number of stage of 200 to 1000 stages, for example, in the moving direction of the sample S and an output of the summation. Furthermore it is possible to allocate the number of stages in the moving direction so as to set the shield area A1 matching with an annealing time necessary for the phosphor 3b, by the TDI sensor.

Since the shield moving mechanism 5 changes the position of the shield area A1 at a constant interval, it is possible to move the shield area A1 automatically and periodically.

Then, a second embodiment of an X-ray transmission inspection apparatus according to the present invention will be described with reference to FIG. 2. In the following descriptions, components the same as those in the first embodiment are denoted by the same reference numerals and descriptions thereof will be omitted.

Figure 2:
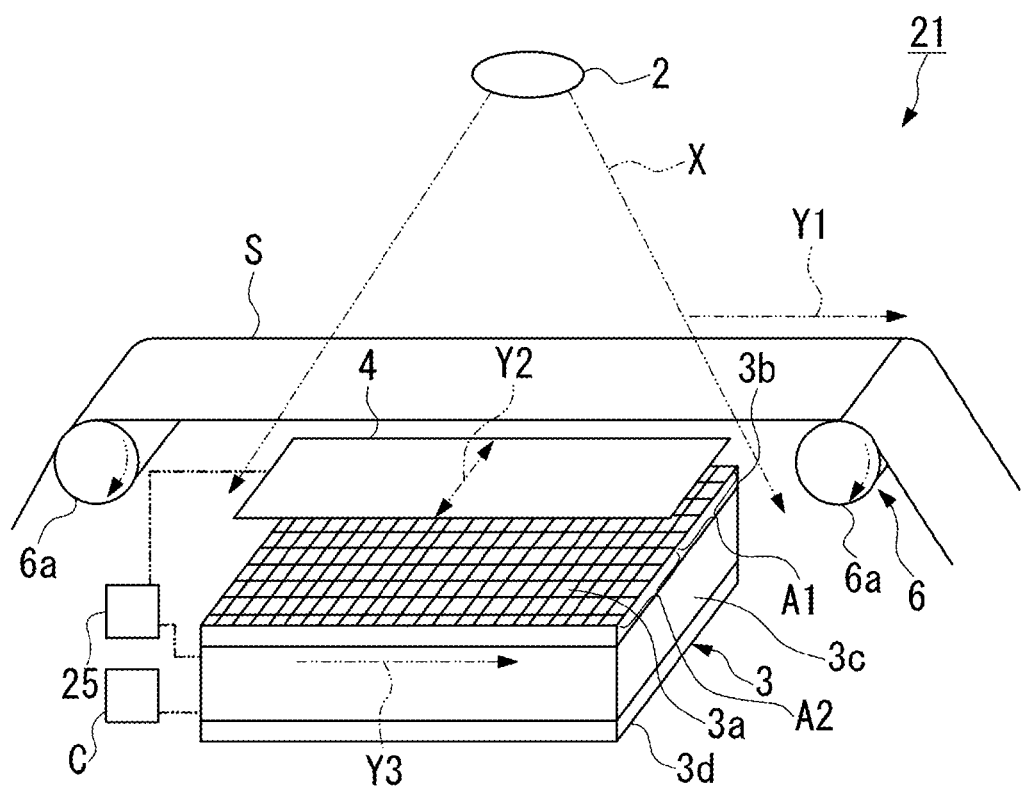
FIG. 2 is an overall configuration diagram schematically illustrating a second embodiment of an X-ray transmission inspection apparatus according to the present invention.

The second embodiment is different from the first embodiment in that in the first embodiment, the shield moving mechanism 5 moves the shield member 4 in the longitudinal direction of the sample S, but in an X-ray transmission inspection apparatus 21 according to the second embodiment, the width of the detection surface 3a is set to be larger than the width of the sample S and the shield moving mechanism 25 enables the shield member 4 to be relatively moved in a direction orthogonal to the extension direction of the sample S, as illustrated in FIG. 2.

That is, in the second embodiment, a shield moving mechanism 25 enables the detector 3 and the shield member 4 to be mutually moved in the direction orthogonal to the extension direction of the sample S and thus the shield moving mechanism 25 sets the detection area A2 to be disposed just under the sample S constantly and moves the detector 3 and the shield member 4 such that the shield area A1 is disposed at a portion out of a portion just under the sample S. In this case, even though the shield area A1 is moved, the number of stages of the TDI sensor in the moving direction of the sample S is maintained constantly all the time.

In the X-ray transmission inspection apparatus 21 according to such the second embodiment, since the width of the detection surface 3a is set to be larger than the width of the sample S and the shield moving mechanism 5 enables the shield member 4 to be moved relative to the detector 3 in the direction orthogonal to the extension direction of the sample S, it is possible to move the shield area A1 regardless of changing the number of stages of the TDI sensor.

The technical range of the present invention is not limited to the above-described embodiments and various changes may be applied within a range without departing from the purpose of the present invention.

For example, in the first embodiment, the shield moving mechanism moves only the shield member, but may move only the detector or both of the shield member and the detector and change a position of the detector relative to the shield member.

According to an aspect of the present invention, an X-ray transmission inspection apparatus is provided with a shield member and a shield moving mechanism, the shield member blocks some of X-rays and partially forms a shield area from X-rays on a detection surface, and the shield moving mechanism moves the shield member relative to the detector and enables change of a position of the shield area. Thus, the detection area and the shield area on the detection surface which are irradiated with an X-ray are shifted with time by moving the shield member, and thus it is possible to restore luminous intensity of a phosphor in the shield area. Accordingly, it is also possible to reduce a downtime of an apparatus and to obtain a long lifespan of a detector in the apparatus operating full time around the clock.

What is claimed is:

1. An X-ray transmission inspection apparatus comprising:
    an X-ray source configured to irradiate a sample with an X-ray;
    a detector configured to be disposed on a side opposite to the X-ray source with respect to the sample and to detect the X-ray which is transmitted through the sample using a phosphor;
    a shield member configured to be arranged to face a detection surface of the detector and to block a part of the X-ray to partially form a detection area and a shield area on the detection surface, the detection area on which the X-ray is irradiated, and the shield area being shielded from the X-ray; and
    a shield moving mechanism that operates to perform a switching sequence including:
        moving the shield member relative to the detector from a first position to a second position, wherein the first position is a position at which the detection surface of the detector is divided into an initial detection area and an initial shield area, and wherein the second position is a position at which at least a part of the initial detection area becomes a new shield area and at least a part of the initial shield area becomes a new detection area; and
        maintaining the shield member at the second position for a time period that is long enough to restore the phosphor used in the detector within the initial detection area while allowing the detector to detect the X-ray with the detection surface that has become the new detection area.

2. The X-ray transmission inspection apparatus according to claim 1 further comprising:
    a sample moving mechanism configured to move the sample having a belt shape in a longitudinal direction of the sample,
    wherein the detector is configured by a TDI sensor, and
    wherein the shield moving mechanism is configured to move the shield member relative to the detector in the longitudinal direction of the sample.

3. The X-ray transmission inspection apparatus according to claim 1 further comprising:
    a sample moving mechanism configured to move the sample having a belt shape in a longitudinal direction of the sample,
    wherein the detector is configured by a TDI sensor,
    wherein the detection surface is set to have a width which is larger than that of the sample, and
    wherein the shield moving mechanism is configured to move the shield member relative to the detector in a direction orthogonal to the longitudinal direction of the sample.

4. The X-ray transmission inspection apparatus according to claim 1,
    wherein the shield moving mechanism is configured to change a position of the shield area at a constant interval.

5. The X-ray transmission inspection apparatus according to claim 1,
    wherein the switching sequence further includes:
        moving, after the time period has elapsed, the shield member relative to the detector from the second position to a third position at which at least a part of the new detection area becomes another shield area and at least part of the new shield area becomes another detection area.

6. The X-ray transmission inspection apparatus according to claim 5, wherein the another shield area corresponds to the initial shield area, and wherein the another detection area corresponds to the initial detection area.

* * * * *